United States Patent [19]

Wilharm et al.

[11] Patent Number: 5,162,559
[45] Date of Patent: Nov. 10, 1992

[54] SILYLATION REAGENTS FOR PREPARING BINDERS WHICH ARE SOLUBLE IN AQUEOUS ALKALI AND CONTAIN SILANYL GROUPS IN THE SIDE CHAIN

[75] Inventors: Peter Wilharm, Wiesbaden; Juergen Fuchs, Floersheim-Wicker, both of Fed. Rep. of Germany

[73] Assignee: Hoechst Aktiengesellschaft, Frankfurt am Main, Fed. Rep. of Germany

[21] Appl. No.: 332,031

[22] Filed: Apr. 3, 1989

[30] Foreign Application Priority Data

Apr. 2, 1988 [DE] Fed. Rep. of Germany ....... 3811241

[51] Int. Cl.$^5$ ............................ C07F 7/08; C07F 7/10; C07F 7/18
[52] U.S. Cl. .................... 556/411; 556/413; 556/414; 556/410; 556/419; 556/420; 556/427; 556/428; 556/430; 548/955; 549/214; 549/215
[58] Field of Search ............... 556/411, 430, 413, 427, 556/428, 419, 420, 414, 410; 549/214, 215; 548/955

[56] References Cited

U.S. PATENT DOCUMENTS

| | | | |
|---|---|---|---|
| 4,464,455 | 8/1984 | Yoneda et al. | 430/270 |
| 4,481,049 | 11/1984 | Reichmanis et al. | 156/643 |
| 4,481,279 | 11/1984 | Naito et al. | 430/280 |
| 4,544,729 | 10/1985 | Nate et al. | 528/28 |
| 4,551,417 | 11/1985 | Suzuki et al. | 430/316 |
| 4,871,646 | 10/1989 | Hayase et al. | 556/430 X |

FOREIGN PATENT DOCUMENTS 2217744 10/1973 Fed. Rep. of Germany ...... 556/430 UX

OTHER PUBLICATIONS

Patent Abstract, 83-792423/42, G06 A89 L03 P83, Hita Oct. 3, 1982, J5 8153-931-A.
Patent Abstract, Hita, G06, 85-002102/01, J5 9061-83-1-A.
Patent Abstract, Fuit, G06, 84-209630/34, J5 9121-04-2-A.
Patent Abstract, HITA, G06, 85-052484/09, J6 0008-839-A.
Patent Abstract, HITA, G06, 86-186160/29, J6 1118-745-A.
Patent Abstract, HITA, G06, 86-261588/40, J61189-533-A.
Patent Abstract, HITA, G06, 87-070526/10, J6 2025-744-A.
Patent Abstract, NIDE, G06, 87-254666/36, J62177-005-A.
Patent Abstract, OKID, G06, 87-003963/01, J6 1264-342-A.
Patent Abstract, FUIT, G06, 84-216055/35, J5 9125-729-A.
Patent Abstract, FUIT, G06, 84-216056/35, J5 9125-730-A.

*Primary Examiner*—Paul F. Shaver
*Attorney, Agent, or Firm*—Foley & Lardner

[57] ABSTRACT

A silylation reagent is useful for preparing binders which are soluble in aqueous alkali and contain silanyl groups in the side chain, comprises a compound having the formula I

$$(A-B_n)_mC \qquad (I)$$

wherein
A denotes a silanyl group containing at least 2 silicon atoms in total linked to each other, but not more than 3 silicon atoms linked to each other in an unbranched chain of silicon atoms;
B denotes a bridging group;
C denotes a functional group which is capable of forming a covalent bond with an aromatic, aliphatic or cycloaliphatic hydroxyl group;
n denotes 0 or 1; and
m denotes 1 or 2.

Binders prepared with the silylation reagents described are soluble in aqueous alkali and exhibit a high resistance to plasma etching and a high storage stability, and are resistant to rediation with a wavelength of greater than 300 nm.

18 Claims, 2 Drawing Sheets

SILYLATION REAGENTS FOR PREPARING BINDERS WHICH ARE SOLUBLE IN AQUEOUS ALKALI AND CONTAIN SILANYL GROUPS IN THE SIDE CHAIN

BACKGROUND OF THE INVENTION

This invention relates to silylation reagents which are suitable for the preparation of binders carrying silanyl groups in the side chain and soluble in aqueous alkali.

In the submicron region, in particular, with increasing resolution and at the same time decreasing focussing tolerance for structuring substrates with complicated topography, microlithography requires the use of multi-layer systems. The two-layer system is preferred because of simpler processability.

Usually the substrate has a complicated topography which is due to process steps which are standard in the manufacture of microelectronic circuits such as, for example, metallization, oxide deposition, epitaxy etc.

In the two-layer process, the topographically uneven substrate is leveled by a so-called planarization layer. As materials for the planarization layer, use is typically made of polymers which can be satisfactorily etched in the subsequent plasma etching process.

The actual resist layer, which is exposed through an image, is applied to the planarization layer. After the development of the exposed or unexposed regions (depending on the process used, i.e., positive- or negative-working), the resist layer which has not been removed acts as a mask for plasma etching the planarization layer thereunder which is now not covered by the image. The resist layer must therefore be resistant to plasma etching, in particular to oxygen plasmas, and at the same time must make highly resolved structures possible. The preparation of highly resolved structures by means of multi-layer processes, in particular two-layer processes, is described in detail by E. Reichmanis, G. Smolinsky and C. W. Wilkins in Solid State Technology, August 1985, page 130. Photosensitive layers on planarization layers are reviewed by Y. Onishi et al. in SPIE, vol. 539, Advances in Resist Technology and Processing II, page 62.

The resistance of binders to plasma etching, in particular the resistance to oxygen plasmas, can be achieved by incorporating metal atoms (for example Si, Ge, Sn, Ti). In practice, the use of silicon has proved successful: silicon-containing compounds are relatively readily accessible synthetically, have in general a low toxicity and do not represent a source of contamination in processes for manufacturing microelectronic circuits. Hitherto known silicon-containing binders which contain polysiloxane groups bound to conventional binders are described in U.S. Pat. No. 4,481,049.

Binders of this type, however, have too low a glass transition temperature so that it is not possible to prevent the resist structures flowing under thermal load, such as may occur, for example, in plasma etching processes. As a consequence thereof, it is not possible to prevent a loss of dimensional stability. Binders of this type are also incompatible with other binders, in particular with alkali-soluble binders. In addition, their low lithographic sensitivity and the restriction to irradiation wavelengths in the deep UV light range are disadvantageous.

A polysiloxane which contains disilane units is described by M. Ishikawa et al. in J. Polym. Sci. 21, page 657 (1983). Added to the known low glass transition temperature of polymers containing Si—O—Si groups is, in the case of this compound, also an elaborate synthesis of the silicon-containing monomers necessary for these compounds.

Furthermore, polymers are known which have polysilane groups as a constituent of the main chain and which contain two to six Si atoms linked to each other (EP-A-0,129,834, JP-A-153931/1983, JP-A-061831/1984, JP-A-008839/1985, JP-A-118745/1986, JP-A-189533/1986 and JP-A-025744/1987). Although compounds of this type are resistant to reactive oxygen-ion etching, they are at the same time active as chromophores towards deep UV light, i.e., they can be cleaved by light of these wavelengths. This makes them disadvantageous for use in photosensitive mixtures: the irradiation wavelengths are restricted to the deep UV region and are consequently not usable in the current I- and H-line exposure equipment employed for mass production. A further disadvantage is the difficulty of synthesizing these compounds, since alkali-metals have to be used in a highly reactive form. At the same time, there is no immediate guarantee that polymers will be produced which are soluble in aqueous alkali. This would entail development of a solvent, which is not considered feasible due to environmental protection standards. In addition, they are not compatible with cresol-formaldehyde-novolak resins since mixtures of these components immediately separate before they are able to form a uniform film on the base (substrate), or on the planarization layer.

Binders for photosensitive mixtures which contain monosilane groups (—SiR$_3$) are described in EP-A-0,096,596. Disadvantages of the compounds of this type are, inter alia, a complicated monomer and also polymer synthesis. By introducing only one silicon atom per monomer unit, it is possible to achieve the silicon content of the binders required as a minimum for an appropriate resistance to plasma etching only with difficulty, if at all. A serious disadvantage is that these binders permit only an image differentiation due to development with organic solvents.

DE-A-2,217,744 describes polymeric binders which also contain —SiR$_3$— groups, but in this case are produced by a polymer-analogous reaction of polymeric binders with reactive silicon-containing compounds, or by copolymerization. Whether these compounds are resistant to plasma etching is not evident from this publication, but they are claimed to improve the adhesion to substrates. Due to the chemical reactivity of Si—X bonds, the storage life of these compounds is very limited and under certain circumstances a post-curing is possible.

Binders carrying methylene-linked Si fragments are described as constituents of resist systems in JP-A-177005/1987. These can, however, be prepared only by means of a multi-stage and elaborate synthesis.

Si-containing binders in which the phenolic hydroxyl functions are linked to silicon via ester or iminoester functions are described in JP-A-264342/1986. A disadvantage is, however, that the silicon-ester or silicon-iminoester units described may also be decomposed at the wavelengths used for the photolysis of the naphthoquinonediazides or benzoquinonediazides added, and are split off. A further disadvantage of the compounds cited is their chemical instability towards, for example, hydrolytic decomposition, which has an unfavorable effect on the storage stability. It is furthermore disadvantageous that the multi-stage synthesis of the compounds cited is difficult to reproduce and proceeds with low overall yields.

Binders to which monomers are added, containing disilanyl units to impart resistance to plasma etching to the host polymer, are described in U.S. Pat. Nos. 4,481,279 and 4,464,455, as are similar compounds in JP-A-125729/1984, 125730/1984 and 121042/1984. The disilanyl compounds added to the binder are anchored in the polymer matrix by ionizing radiation. Before the development step by means of reactive ion etching using oxygen, the disilane is removed from the unexposed region with the aid of a vacuum process, for example. The disadvantage of the process is, inter alia, that the differentiation in terms of image is unsatisfactory because silicon-containing monomers are still present in the unexposed regions and can only be removed inadequately, even by the above-mentioned vacuum process.

There presently exists a need for a silylation reagent which can be utilized successfully for preparing binders of high purity which will have the following properties: An adequate solubility in aqueous alkali, a very high resistance to plasma etching in the case of reactive ion etching with oxygen, a long storage stability, and a high resistance to radiation so that exposure to an image of photosensitive mixtures can be undertaken (I- and H-exposure equipment, wavelength greater than 300 nm).

OBJECTS OF THE INVENTION

It is therefore an object of the present invention to provide silylation reagents with which binders soluble in aqueous alkali can be modified in a manner so that they have an adequate resistance to plasma etching relative to reactive ion etching, in particular with oxygen.

It is another object of the invention that the binder prepared with the claimed silylation reagent remain soluble in aqueous alkali even after modification, i.e., can be developed aqueously.

It is a further object that the binder prepared with the claimed silylation reagent not decompose hydrolytically or in any other chemical manner, so that a long storage life is guaranteed.

Another object is to permit exposure with modern exposure equipment without starting a decomposition of the polymer initiated by this radiation.

A further object is to provide a silylation reagent for preparing binders which are not volatile.

Another object of the invention is that both the monomers and binders ultimately modified with said monomers be easy to prepare and be of high purity.

SUMMARY OF THE INVENTION

These and other objects are achieved by providing a silylation reagent which comprises a compound having the formula I $$(A-B_n)_m C \qquad (I)$$

wherein

A denotes a silanyl group containing at least 2 silicon atoms in total linked to each other, but not more than 3 silicon atoms linked to each other in an unbranched chain of silicon atoms;

B denotes a bridging group;

C denotes a functional group which is capable of forming a covalent bond with an aromatic, aliphatic or cycloaliphatic hydroxyl group;

n denotes 0 or 1; and m denotes 1 or 2.

Binders prepared with the silylation reagents according to the invention are resistant to radiation of a wavelength greater than 300 nm.

The binders contain the silanyl groups on which the silylation reagents of the general formula I are based in the side chain. The term "side chain" means that the silanyl groups are not a constituent of the main polymer chain of the binder. This would not be possible in view of the method of introducing these groups into the binder, since the binder is a polymer even before the silanyl groups are introduced.

DETAILED DESCRIPTION OF THE PREFERRED EMBODIMENTS

The invention provides a silylation reagent as a monomer of the general formula I $$(A-B_n)_m C \qquad (I)$$

wherein

A denotes a silanyl group containing at least 2 silicon atoms in total linked to each other, but not more than 3 silicon atoms linked to each other in an unbranched chain of silicon atoms;

B denotes a bridging group;

C denotes a functional group which is capable of forming a covalent bond with aromatic and/or aliphatic or cycloaliphatic hydroxyl groups;

n denotes 0 or 1; and m denotes 1 or 2.

Silanyl groups having the formula II are suitable as the group A:

$$-\underset{\underset{a_3}{|}}{\overset{\overset{a_1}{|}}{Si}}-a_2, \qquad (II)$$

wherein $a_1$, $a_2$, $a_3$ each independently denote R, —SiR$_3$ and —Si$_2$R$_5$, with the proviso that at least one of $a_1$, $a_2$ or $a_3$ is —SiR$_3$ and not more than one of $a_1$, $a_2$ or $a_3$ is —Si$_2$R$_5$; and each R independently denotes (C$_1$-C$_3$)-alkyl, in particular methyl, or aryl, in particular phenyl.

In particular, those silanyl groups are preferred which contain two, three or four silicon atoms and/or contain (C$_1$-C$_3$)alkyl, in particular methyl, as radical R.

Particularly preferred are the following silanyl groups: —SiR(SiR$_3$)$_2$, —Si(SiR$_3$)$_3$ and —(SiR$_2$)$_2$—SiR$_3$.

Bridging groups having the formula III are suitable as the group B:

$$-(b_1)_r-(X)-(b_2)_s- \qquad (III).$$

wherein $b_1$ denotes ($C_1$-$C_4$)alkylene, in particular $C_2$-alkylene, or a group containing at least one C—C double bond and resulting from 1,4-cyclo-addition (Diels-Alder) reaction of an alkadienylene, in particular a cycloalkadienylene containing a total of at least 4 carbon atoms, in particular cyclopentadienyl, with a dienophile;

X denotes a single bond, —O—, —S—, —$SO_2$—, —NH—, —$NR^1$—, wherein $R^1$ is a ($C_1$-$C_3$)alkyl, $b_2$ denotes arylene, in particular naphthylene and phenylene, optionally substituted by ($C_1$-$C_3$)alkyl, ($C_1$-$C_3$)alkoxy, in particular by methyl and in the ortho position to the bond which carries the functional group, or cycloalkylene, in particular cyclohexylene; and also r, s each denote 0 or 1, with the proviso that for the bridging group B the sum of the values of r and s is at least 1.

Provided $b_2$ is configured in accordance with the above specifications and X represents a single bond, $b_1$ is an alkylene group preferably containing two or more carbon atoms, in particular a $C_2$-alkylene group. Preferably, $b_1$ is bound to group A.

As group C, suitable functional groups include thiol, hydroxyl, amino, epoxy, optionally bound via an alkyleneoxa, in particular methyleneoxa group, and also aziridino and carboxyl, their derivatives such as esters, chlorides, amides, anhydrides or lactones and lactams, but also isocyanate or carbodiimide.

In particular, those functional groups are preferred which react by addition in a reaction with hydroxyl groups of the binders. Of these, those are preferred in which no amino groups are formed during the addition reaction.

Almost all the functional groups C are monovalent, i.e., the groups A and B are contained once in the silylation reagent of the general formula I (m=1 and n=1). If m=2 and n=1, a bivalent functional group C, for example a carbodiimide, is involved.

In particular if lactones or lactams are used as functional groups C, then n=0 (m=1). Of the lactones and lactams, the β-lactones or β-lactams, the δ-lactones or δ-lactams, and the γ-lactones or γ-lactams are preferred. In particular, the corresponding lactones are preferred.

Of the anhydrides, cyclic anhydrides are preferred in particular, since these, in contrast to the open-chain compounds, react according to an addition pattern and do not initiate a substitution reaction. Very particularly preferred is the maleic anhydride group. An anhydride that is a dienophile can be reacted with a diene in a 1,4-cycloaddition (Diels-Alder) reaction, and the resultant anhydride will be linked via a suitable bridging group B to the silanyl group A. The anhydride group may, however, also be linked to a diene fragment capable of cycloaddition.

Of the preferred functional groups C, mention must furthermore be made of the epoxy group bound to the silanyl group via an alkyleneoxa group, which epoxy group is linked both via $b_1$, provided s=0 and X is either a less preferred single bond or an group, and also via $b_2$, provided s=1, X is preferably a single bond, and $b_2$ is phenylene.

The isocyanate group is also preferred. It is particularly preferably linked to $b_1$, provided s=0, and also to $b_2$, provided The carbodiimides which have also been mentioned as functional groups C are allowable for m=2 and n=1. These are obtained by reaction of two isocyanate groups with each other to split off $CO_2$. Consequently, all the remarks which are made for the isocyanate groups are also valid for the carbodiimide groups. The latter are preferably linked to the silanyl group via bridging unit $b_1$, provided s=0 and X represents a single bond.

In principle, however, silylation reagents which contain isocyanate groups are preferable to those which contain carbodiimide groups since the former yield products which are more resistant to hydrolytic attack.

The preparation of compounds which contain isocyanate groups is described by S. Patai, The Chemistry of Cyanates and Their Thio Derivatives, Part 2, page 619 ff. The functional groups are also described which are in principle capable of reacting with this group, in particular through an addition reaction.

Furthermore, a large number of functional groups are known to the person skilled in the art which make possible a covalent linkage between silylation reagent and binder. Such groups are described by H. A. Staab in Angew. Chem. 74, 407 (1962).

In addition, those functional groups are also suitable which are known, for example, in peptide chemistry for bond formation and are described, inter alia, by K. Takeda, K. Tsuboyama, K. Yamaguchi and H. Ogura in J. Org. Chem. 50, 273 (1985) or by T. Mukaiyama, M. Usui, E. Shimada and K. Saigo in Chem. Lett. 741 (1975).

These are not, however, preferred since they react with substitution during the linking of the covalent bond between the silylation reagent and the hydroxyl group of the binder.

The silylation reagents claimed according to the invention are resistant to UV radiation, in particular to radiation in the range of a wavelength greater than 300 nm, and preferred representatives are the following compounds:

2-(pentaalkyl-or-aryldisilanyl)-($C_1$-$C_4$)alkyl isocyanates, 2-[tris(trialkyl- or -arylsilyl)silanyl]-($C_1$-$C_4$)alkyl isocyanates, 2-[bis(trialkyl- or -arylsilyl)silanylalkyl]-($C_1$-$C_4$)alkyl isocyanates and also 2-(heptaalkyl- or -aryltrisilanyl)-($C_1$-$C_4$)alkyl isocyanates. Among the representatives of these monomers, particularly preferred are those whose silanyl radical carries alkyl groups, in particular methyl. As a link, the ethylene group is particularly preferably employed in these compounds.

Preferred representatives of those compounds which contain epoxy groups as functional groups are: 4-(ω-pentaalkyl- or -aryldisilanyl($C_1$-$C_4$)alkyl)-phenyl 2',3'- epoxypropyl ethers, 4-[ω-tris(trialkyl- or -aryl-silyl)-silanyl($C_1$–$C_4$)alkyl]-phenyl 2′,3′-epoxypropyl ethers, 4-[ω-bis(trialkylsilyl)alkylsilanyl($C_1$–$C_4$)-alkyl]-phenyl 2′,3′-epoxypropyl ethers, and also 4-[ω-heptaalkyl-trisilanyl($C_1$–$C_4$)alkyl]-phenyl 2′,3′-epoxypropyl ethers. Also suitable are the corresponding compounds whose silanyl radical is situated in position 2 instead of position 4 on the benzene ring with respect to the 2′,3′-epoxypropyloxy group. The ($C_1$–$C_4$)-alkylene bridge through which the silanyl radical is linked, both in position 2 and also preferably in position 4, is particularly preferably at least a $C_2$-alkylene radical, $C_2$-alkylene also being the preferred radical of this series. The silanyl radical is then joined at position 2 of the $C_2$-alkylene radical. In this compound class, those compounds are also particularly preferred in which alkyl groups are present in the respective silanyl radicals. The preferred alkyl group is methyl.

The aromatic unit in the bridging group of the compounds described here may also be substituted by alkyl and alkoxy. This embodiment is, however, not preferred.

Preferred representatives of Diels-Alder products are: (2,3)-endo-7-anti-(pentaalkyl- or -aryldisilanyl)-bicyclo[2.2.1]hept-5-ene-2,3-dicarboxylic anhydride, (2,3)-endo-7-anti-[tris(trialkyl- or -arylsilyl)silanyl]-bicyclo[2.2.1]hept-5-ene-2,3-dicarboxylic anhydride, (2,3)-endo-7-anti-[bis(trialkyl- or -arylsilyl)alkylsilanyl]-bicyclo[2.2.1]hept-5-ene-2,3-dicarboxylic anhydride, (2,3)-endo-7-anti-[heptaalkyl- or -aryltrisilanyl]-bicyclo[2.2.1]hept-5-ene-2,3-dicarboxylic anhydride. Particularly preferred are compounds in which alkyl groups are present in the respective silanyl radical. The preferred alkyl group is methyl.

Of the lactams or lactones, the following compounds are preferred:

3-(pentaalkyl- or -aryldisilanyl)lactones and lactams, tris(trialkyl- or -arylsilyl)silanyl lactones and lactams, bis(trialkyl- or -arylsilyl)alkylsilanyl lactones and lactams, and also heptaalkyltrisilanyl lactones and lactams. Particularly preferred are those compounds in which alkyl groups are present in the respective silanyl radicals. The preferred alkyl group is methyl.

Lactones are particularly preferred, in particular β-propiolactones, β- and γ-butyrolactones, β-, γ- and δ-valerolactones, γ- and δ-caprolactones.

Of the silylation reagents which contain carbodiimide as a functional group, those compounds should be mentioned which may also contain isocyanate groups. In comparison with these, those compounds containing carbodiimide are less preferred.

Furthermore, functional units are preferred whose bridging group contains carbamic acid units as X. The actual functional groups may be bound directly in ester fashion to these units, but the units may also function as a connecting link in the bridging group, i.e., not be connected directly to the functional groups.

The following should be mentioned as examples: N-[ω-(pentaalkyl- or -aryldisilanyl)-($C_1$–$C_4$)-alkyl]carbamic acid-2′,3′-epoxypropyl esters, N-{ω-[tris(trialkyl- or -arylsilyl)silanyl]-($C_1$–$C_4$)-alkyl}carbamic acid-2′,3′-epoxypropyl esters, N-{ω-[bis(trialkyl- or -arylsilyl)alkylsilanyl]-($C_1$–$C_4$)-alkylcarbamic acid -2′,3′-epoxypropyl esters, and N-[ω-(heptaalkyl- or -aryldisilanyl)-($C_1$–$C_4$)-alkyl]carbamic acid-2′,3′-epoxypropyl esters.

Of these, those are preferred which contain alkyl groups. A preferred alkyl group is methyl. Of the bridging ($C_1$–$C_4$)-alkylene units, those are preferred which contain $C_2$-alkylene, so that the position "ω" may be more precisely defined as position 2. In addition to these, the following are particularly preferred: N-isocyanatophenyl-carbamic acid ω-silanyl-($C_1$–$C_4$)-alkyl esters, in each case pentaalkyldisilanyl, tris(trialkylsilyl)silanyl, bis(trialkylsilyl)alkylsilanyl and heptaalkyltrisilanyl and also the corresponding arylsilanyl groups being understood as silanyl, as in the previous examples.

As ($C_1$–$C_4$)-alkylene radicals, those are preferred which contain $C_2$-alkylene, so that the position "ω" may be more precisely defined as position 2. Very particularly preferred are compounds of this type which carry the isocyanate groups in position 4 of the phenyl radical, of which those are particularly employed whose phenyl radical is additionally substituted in position 3 by alkyl, in particular by methyl. The alkyl substituents of the silanyl groups are preferably methyl.

The silanyl compounds forming the basis of these silylation reagents must be halogenated, in particular chlorinated, in order to be able to react with the bridging groups described. Mixtures of compounds of this type are produced in industrial quantities as byproducts of the so-called direct synthesis, as it is described, for example, by R. Schliebs and J. Ackermann in Chem. i. u. Zt. 21, 121 (1987). Furthermore, compounds of this type can be systematically synthesized in good yields starting from the simplest silicon compounds. Comprehensive details are to be found in the following publications: M. Kumada and K. Tamao in Adv. Organomet. Chem. 6, 19 (1968) and E. Hengge in Topics in Current Chemistry 51, 1 (1974).

Binders carrying the silanyl groups claimed according to the invention in the side chains all have the properties required according to the object. In particular, the following should be mentioned:

They can be prepared in a simple manner and in high purity and have an adequate solubility in aqueous alkali, a very high resistance to plasma etching, for example, in the case of reactive ion etching with oxygen, a surprisingly long storage stability, and also a high resistance to radiation so that exposure to an image of photosensitive mixtures can be undertaken (I- and H-exposure equipment, wavelength greater than 300 nm), which could not be expected with the prior art.

The following examples are intended to illustrate the invention. The binders prepared for comparison and containing only monosilane groups do not have the advantages which are achievable with the monomers prepared according to the invention. In particular, compared with those which are reacted with the silylation reagents according to the invention, the binders which contain monosilane groups do not show adequate resistance to plasma etching, with the proviso that in both cases the molar ratios of the reaction starting products are identical and in the case of the binders according to the invention, in particular, an adequate resistance to plasma etching is achieved.

EXAMPLE 1

Preparation of 2-(pentamethyldisilanyl)ethyl isocyanate 50 g of 2-(pentamethyldisilanyl)ethylamine hydrochloride is suspended in 100 ml of dry toluene in a 250 ml two-neck flask fitted with a gas inlet tube and reflux condenser. A powerful stream of gaseous phosgene is then passed through the solution while stirring. At the same time the solution is heated to boiling. The conversion of the hydrochloride to the isocyanate is terminated when a clear toluene solution has been produced. Subsequently, the excess toluene is distilled off in a water-jet vacuum and the residue left behind is fractionated in an oil-pump vacuum.

The yield is 42 g (95% of theory) and the boiling point is found to be 48° C./0.1 mm Hg.

The purity is determined by gas chromatographic analysis and is >99%.

Figure 1:
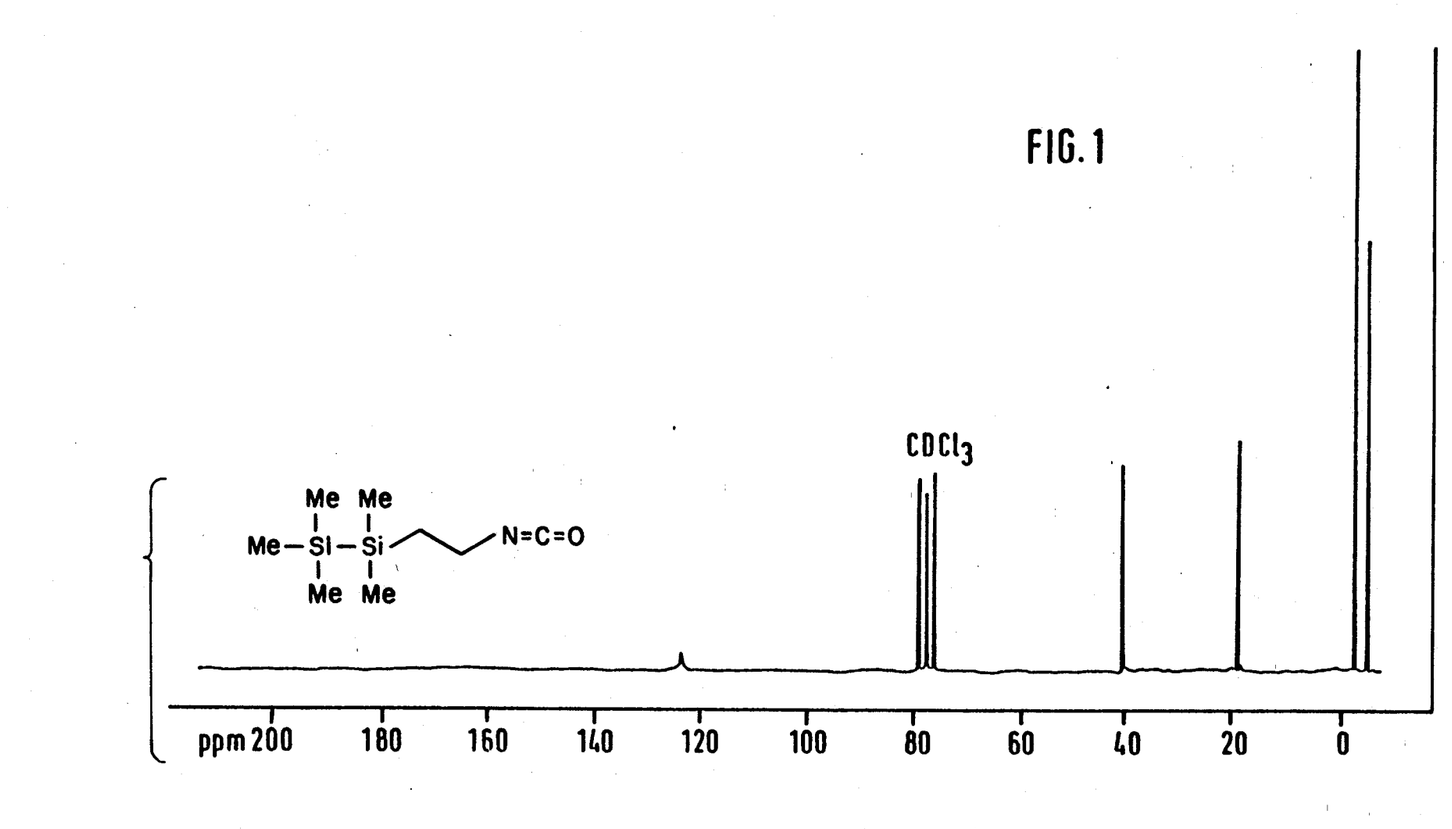
FIG. 1 is a $^{13}C$ NMR spectrum of the silylation reagent according to the invention, produced by the method of Example 1.

A $^{13}$C NMR spectrum (22.5 MHz, CDCl$_3$ as solvent and reference) yields the following peaks (see FIG. 1):

$\delta = 122.8$ ppm (—NCO), $\delta = 40.2$ ppm (N—CH$_2$—), $\delta = 18.8$ ppm (Si—CH$_2$—)

$\delta = -2.3$ ppm (SiMe$_3$)

$\delta = -4.5$ ppm (—SiMe$_2$—).

The starting product, 2-(pentamethyldisilanyl)ethylamine hydrochloride is prepared as follows:

A solution of 14.7 g of aluminum trichloride (anhydrous) in 50 ml of diethyl ether is added dropwise in 10 min to 4.2 g of lithium aluminum hydride in 50 ml of diethyl ether in a 250 ml three-neck flask under an argon atmosphere. Subsequently, stirring is continued for a further 30 min and then 15.4 g of pentamethyldisilanylacetonitrile is added dropwise in 1 h and the solution is heated for 1 h under reflux.

Next, hydrolysis is carefully carried out dropwise with 100 ml of 20% hydrochloric acid with ice cooling. In this process, the hydrochloride precipitates as a colorless crystalline substance. The crystals are filtered off by suction, dried in vacuo and recrystallized from a small amount of tetrahydrofuran. The yield is 56% after the recrystallization.

A $^{13}$C NMR spectrum (22.5 MHz, CDCl$_3$ as solvent and reference) yields the following peaks:

$\delta = 37.6$ ppm (N—CH$_2$—), $\delta = 14.3$ ppm (Si—CH$_2$—), $\delta = -2.3$ ppm (—SiMe$_3$), $\delta = -4.6$ ppm (—SiMe$_2$—)

The starting compound used for this purpose, pentamethyl-disilanylacetonitrile, can be prepared according to an instruction by M. Kumada et al. in J. Organomet. Chem. 5, 226 (1966).

EXAMPLE 2

Preparation of tris(trimethylsilyl)silanyl-β-ethyl isocyanate

The compound is prepared from tris(trimethylsilyl)-silanyl-β-ethylamine hydrochloride analogously to the method described in Example 1.

The distillative purification of the crude product in a high vacuum with the aid of a bulb tube apparatus yields colorless crystals.

Figure 2:
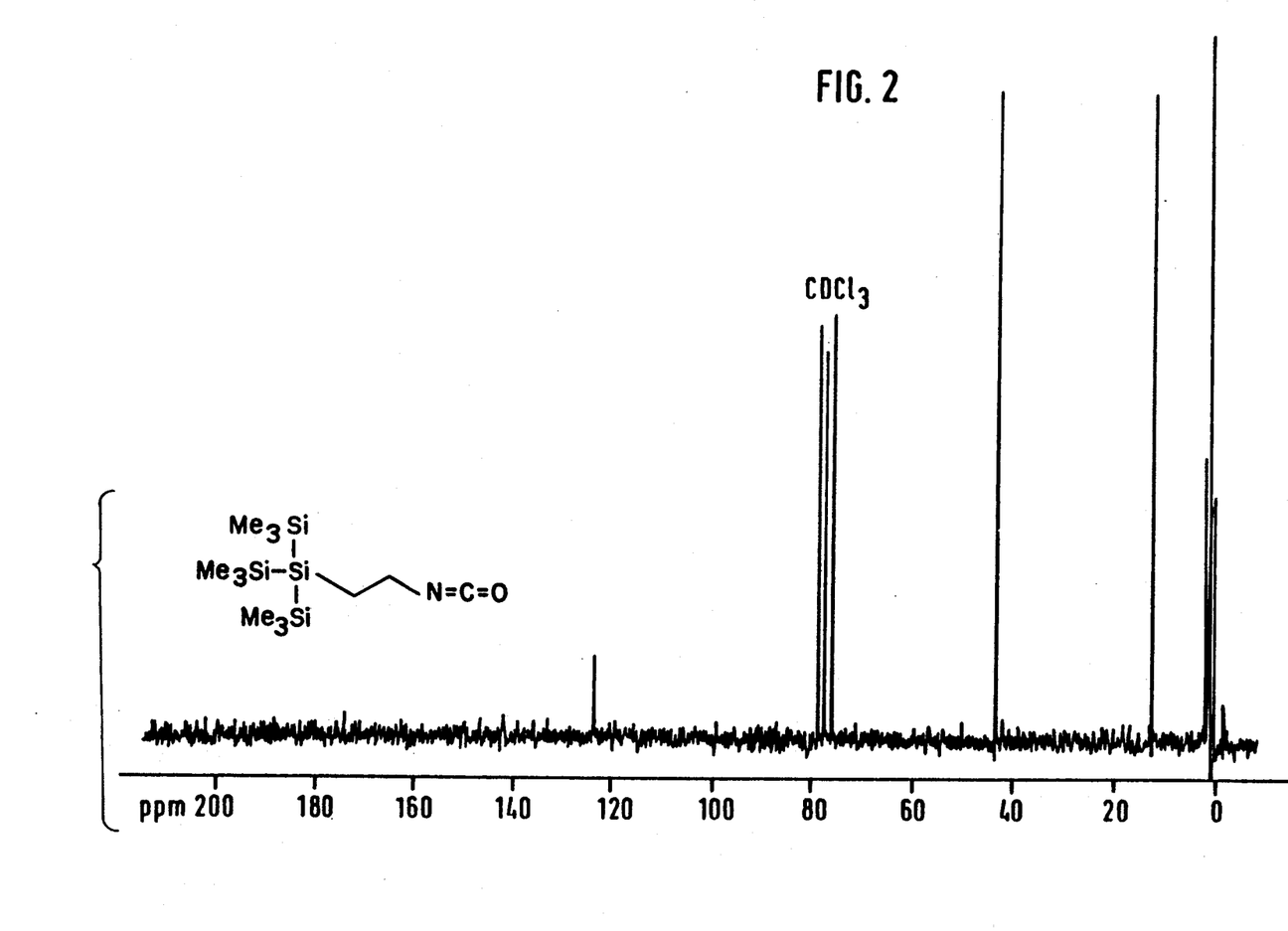
FIG. 2 is a $^{13}C$ NMR spectrum of the silylation reagent according to the invention, produced by the method of Example 2.

A $^{13}$C NMR spectrum (22.5 MHz, CDCl$_3$ as solvent and reference) exhibits the following peaks (see FIG. 2):

$\delta = 122.7$ ppm (—N=C=O)

$\delta = 43.1$ ppm (—CH$_2$—NCO)

$\delta = 12.5$ ppm (Si—CH$_2$—)

$\delta = 1.2$ ppm (—SiMe$_3$)

The elementary analysis yields:
Calculated: C=45.36; H=9.83; N=4.41;
Found: C=45.2; H=9.9; N=4.6.

The starting product used for this purpose, tris(trimethylsilyl)silanyl-β-ethylamine hydrochloride can be prepared by two methods:

1) 4.4 g of 2,2,5,5-tetramethyl-1-aza-2,5-disilacyclopentanylethyl chloride in 20 ml of diethyl ether is added dropwise in the course of 2 h to 0.28 g of lithium chips in 50 ml of dry diethyl ether in a 100 ml flask under an argon atmosphere. Subsequently, stirring is continued for a further 4 h at room temperature and then 5.7 g of tris(trimethylsilyl)chlorosilane is added in one portion. The reaction solution is allowed to stand overnight and then 30 ml of 20% hydrochloric acid are added dropwise with ice cooling. The hydrochloride produced separates as a colorless crystalline substance. The crystals are filtered off by suction and recrystallized from toluene.

Tris(trimethylsilyl)chlorosilane can be produced according to an instruction by H. Bürger, W. Kilian and K. Burczyk in J. Organomet. Chem. 21, page 291 (1970).

2,2,5,5-Tetramethyl-1-aza-2,5-disilacyclopentan-1-ylethyl chloride is prepared from 1,2-bis(chlorodimethylsilyl)ethane and 2-chloroethylamine hydrochloride by a process proposed by F. Z. Basha and J. F. DeBernardis in Tetrahedron Lett., page 5271 (1984).

2) The starting product, tris(trimethylsilyl)silanylacetonitrile, is obtained from tris(trimethylsilyl)-chlorosilane and chloroacetonitrile by a modified process according to the instructions of I. Matsuda, S. Murata and Y. Ishii in J. Chem. Soc. Perkin I, page 26 (1979):

A suspension of 7.2 g of zinc dust in 100 ml of N-methylpyrrolidone is placed, under an argon atmosphere, in a 250 ml three-neck flask fitted with internal thermometer, dropping funnel, protective gas inlet and magnetic stirrer. A mixture composed of 7.6 g of chloroacetonitrile, 28.3 g of tris-(trimethylsilyl)-chlorosilane and 50 ml of N-methylpyrrolidone is added dropwise to the well-stirred suspension in the course of one hour in such a way that the internal temperature does not exceed 60° C. Subsequently, the solution is thermostated at 60° C. for 18 h. To work up, the cooled solution is poured while stirring into 500 ml of ice-water. The precipitated colorless crystalline substance is filtered off by suction and dried in vacuo. The yield is 22 g (76% of theory).

An analytically pure sample is obtained by sublimation at 100° C. in an oil-pump vacuum.

Tris(trimethylsilyl)silanylacetonitrile is reduced to the amine hydrochloride by the process described in Example 1.

A $^{13}$C NMR spectrum of tris(trimethylsilyl)silanyl-β-ethylamine hydrochloride (22.5 MHz, CDCl$_3$ as solvent and reference) exhibits the following peaks:

$\delta = 39.9$ (—CH$_2$—N)

$\delta = 7.2$ (—CH$_2$—Si)

δ=1.1 (—SiMe₃)

The elementary analysis yields:
Calculated: C=40.35; H=10.44; N=4.27;
Found: C=39.9; H=10.5; N=4.1.

EXAMPLE 3

Preparation of 4-(2-pentamethyldisilanylethyl)-phenyl 2',3'-epoxypropyl ether

A mixture of 5.0 g of 4-(2-pentamethyldisilanylethyl)-phenol, 1.8 g of epichlorohydrin, 0.5 g of potassium iodide and 5 g of potassium carbonate is heated for 8 h in a 100 ml flask under reflux while stirring. Subsequently, the precipitated salt and excess potassium carbonate is filtered off and the solution is evaporated down using a rotary evaporator. The oily residue is distilled using a bulb tube apparatus. The product is obtained in a yield of 42%.

A ¹³C NMR spectrum (22.5 MHz, CDCl₃ as solvent and reference) yields the following peaks:

δ=156.3, 137.7, 128.4, 114.4 ppm (aromatic)

δ=68.5 ppm (O—CH₂—)

δ=50.0, 44.2 ppm

δ = 50.0, 44.2 ppm (—C———CH)

δ=29.6, 17.0 ppm (—CH₂—CH₂—)

δ=−2.2 ppm (—SiMe₃)

δ=−4.5 ppm (—SiMe₂—).

The starting product 4-(2-pentamethyldisilanylethyl)-phenol is prepared as follows:

500 ml of dry tetrahydrofuran and 12.4 g of magnesium turnings according to Grignard are placed under an atmosphere of nitrogen in a 1,000 ml three-neck flask fitted with reflux condenser, dropping funnel and internal thermometer. To this, 10 g of 4-(2-bromoethyl)-O-trimethylsilylphenol and subsequently 1 ml of ethylene dibromide are added and the solution is heated while stirring at 60° C. The start of the reaction is recognized by a spontaneous boiling up of the solution even without external heat being supplied. Once the reaction has started, 127 g of 4-(2-bromoethyl)-O-trimethylsilylphenol is added so rapidly dropwise that the solution continues to boil. Subsequently, heating under reflux is continued for a further 1 h. Then 83.4 ml of pentamethylchlorodisilane are added dropwise within 0.5 h and the solution is subsequently heated under reflux for 3 h. Then 300 ml of 3N HCl are added carefully and the reaction solution is evaporated down using a rotary evaporator until 300 ml of tetrahydrofuran have distilled off. The organic phase which separates is separated off and the aqueous phase is extracted with 200 ml of diethyl ether. The combined organic phases are re-extracted with 200 ml of 10% common-salt solution and the organic phase is subjected to vacuum distillation after distillation using a rotary evaporator.

The yield is 61% of theory.

A ¹³C NMR spectrum (22.5 MHz, CDCl₃ as solvent and reference) yields the following peaks:

δ=153.1 ppm (C—OH, aromatic)

δ=137.6, 128.7, 115.3 ppm (aromatic)

δ=29.8 ppm (aromatic—CH)

δ=17.2 ppm (CH₂—Si)

δ=−2.0 ppm (—SiMe₃)

δ=−4.4 ppm (—SiMe₂—)

The starting product 4-(2-bromoethyl)-O-trimethylsilylphenol, can be prepared from 4-(β-bromoethyl)-phenol by reaction with hexamethyldisilazane.

EXAMPLE 4

Preparation of (2,3)-endo-7-anti(pentamethyldisilanyl)-bicyclo[2.2.1-]hept-5-ene-2,3dicarboxylic anhydride 4.0 g of maleic anhydride are dissolved in 50 ml of tetrahydrofuran in a 100 ml flask. 10 g of 5-(pentamethyldisilanyl)cyclopentadiene are slowly added dropwise to this solution with ice cooling in the course of 1 h and is then allowed to stand for a further 6 h at room temperature. Subsequently, the solvent is removed using a rotary evaporator and the residue is recrystallized from cyclohexane. Colorless crystals having a melting point of 85° C. are obtained in a yield of 65%.

A ¹³C NMR spectrum (22.5 MHz, CDCl₃ as solvent and reference) yields the following peaks:

δ=170.9 ppm (C=O)

δ=135.0 ppm (C=C)

δ=56.0, 49.1 ppm (C, cycloaliphatic)

δ=−2.3, −3.3 ppm (—SiMe₃, —SiMe₂—)

The elementary analysis reveals agreement between the values calculated and found.
Calculated: C 57.1%; H 7.5%;
Found: C 57.4%; H 7.6%.

The starting product, 5-(pentamethyldisilanyl)cyclopentadiene, can be prepared from cyclopentadiene and pentamethyldichlorodisilane by a method specified by K. C. Frisch in J. Amer. Chem. 75, page 6050 (1953).

EXAMPLE 5

Preparation of 2-pentamethyldisilanyl-γ-butyrolactone 200 ml of N-methylpyrrolidone and 34.3 g of zinc dust are placed in a 1,000 ml three-neck flask fitted with internal thermometer, cold-drawn precision glass stirrer and dropping funnel. A mixture of 82.5 g of 2-bromo-γ-butyrolactone and 83.4 g of pentamethylchlorodisilane and 100 ml of N-methylpyrrolidone is added dropwise while stirring so that the internal temperature adjusts to 60° C. during the exothermic reaction. Stirring is continued for a further 6 h at this temperature and the reaction mixture is then poured onto 500 g of flaked ice. Once the ice has melted, the organic phase which separates is separated off and the aqueous phase is extracted with 200 ml of cyclohexane. The combined organic phases are distilled off using a rotary evaporator after drying over magnesium sulfate and the residue is distilled in vacuo.

The corresponding 2-pentamethyldisilanyl-β-propriolactone is prepared in an analogous manner.

The yield is 93 g and the boiling point is 75° C./1 mm Hg.

A $^{13}$C NMR spectrum (22.5 MHz, CDCl$_3$ as solvent and reference) yields the following peaks:

$\delta = 179.0$ ppm (C=O)

$\delta = 67.0, 27.6, 24.5$ ppm (aliphatic ring carbon atoms)

$\delta = -2.6$ ppm (—SiMe$_3$)

$\delta = -5.6$ ppm (—SiMe$_2$—)

EXAMPLE 6

Preparation of bis-(2-pentamethyldisilanylethyl)-carbodiimide

This compound is prepared by a process described by T. W. Campbell, J. J. Monagle and V. S. Foldi in J. Amer. Chem. Soc. 84, page 3673 (1962).

20 g of 2-(pentamethyldisilanyl)ethyl isocyanate and 100 mg of 3-methyl-1-phenyl-2,5-dihydrophosphole-1-oxide in 50 ml of toluene are heated while stirring at 50° C. in a 100 ml flask. The generation of carbon dioxide which sets in is monitored with a bubble counter. The generation of carbon dioxide is almost stopped after 5 h. The solvent is distilled off in a water-jet vacuum. The residue left behind is composed of 95% carbodiimide and is sufficiently pure for the reactions described in the simultaneously filed Application Hoe 88/K 023.

The IR spectrum shows a pronounced band at 2,140 cm$^{-1}$ which is typical of the asymmetric N=C=N valency vibration of carbodiimides.

EXAMPLE 7

Preparation of N-[2-(pentamethyldisilanyl)-ethyl]-carbamic acid-2',3'-epoxypropyl ester 10.5 g of 2-(pentamethyldisilanyl)ethyl isocyanate in 50 ml of dry diethyl ether is placed in a 100 ml flask under an atmosphere of nitrogen and 3.7 g of 2,3-epoxy-1-propanol are then added. The mixture is allowed to stand overnight at room temperature and then the solvent is distilled off using a rotary evaporator. The residue is composed of a colorless viscous oil which is sufficiently pure for the reactions with the binders described in the U.S. patent application Ser. No. 07/332,511 of Peter Wilharm et al., (corresponding to German Patent Application P11242.6, filed Apr. 2, 1988), filed Apr. 3, 1989.

EXAMPLE 8

Preparation of N-(3-methyl-4-isocyanatophenyl)-carbamic acid-2-(pentamethyldisilanyl)ethyl ester 17.4 g of toluene-2,4-diisocyanate in 50 ml of tetrahydrofuran are placed in a 250 ml two-neck flask fitted with dropping funnel and internal thermometer under an atmosphere of nitrogen and 17.5 g of 2-(pentamethyldisilanyl)ethanol. 50 ml of tetrahydrofuran are added dropwise thereto in the course of 2 h with ice cooling. The reaction is slightly exothermic and the internal temperature should not exceed 20° C. Subsequently, the reaction solution is stirred for 8 h at room temperature and the solvent is then distilled off using a rotary evaporator. A viscous residue is left which is sufficiently pure for the reactions described in the aforementioned simultaneously filed U.S. patent application Ser. No. 07/332,511.

The starting product, 2-(pentamethyldisilanyl)ethanol, can be prepared according to M. Kumada, N. Imaki and K. Yamamoto in J. Organomet. Chem. 6, page 490 (1966).

EXAMPLE 9 (COMPARATIVE EXAMPLE)

Preparation of 2-(tri-methylsilyl)ethyl isocyanate

The compound is prepared analogously to the method described in Example 1.

A $^{13}$C NMR spectrum (22.5 MHz, CDCl$_3$ as solvent and reference) exhibits the following peaks:

$\delta = 122.5$ ppm (—N=C=O)

$\delta = 39.7$ ppm (N—CH$_2$—)

$\delta = 20.3$ ppm (Si—CH$_2$—)

$\delta = -1.9$ ppm (—SiMe$_3$)

The starting product, 2-(trimethylsilyl)ethylamine hydrochloride, can be prepared according to L. H. Sommer and J. Rockett in J. Amer. Chem. Soc. 73, page 5130 (1951).

EXAMPLE 10 (COMPARATIVE EXAMPLE)

Preparation of N-(3-methyl-4-isocyanato-phenyl)-carbamic acid -2-(trimethylsilyl)ethyl ester The compound is prepared by the method described in Example 8.

A colorless viscous liquid is obtained which is sufficiently pure for the reactions described in the aforementioned simultaneously filed U.S. patent application Ser. No. 07/332,511.

EXAMPLE 11 (COMPARATIVE EXAMPLE)

(2,3)-endo-7-antitrimethylsilyl-bicyclo[2.2.1]hept-5-ene-2,3dicarboxylic anhydride

The anhydride can be prepared according to P. Magnus, P. M. Cairns and J. Moursounidis in J. Amer. Chem. Soc. 109. page 2469 (1987).

The analytical values obtained agree with the values specified in the literature cited.

---

Product from Preparation Example 1

-continued

Product from Preparation Example 2

Product from Preparation Example 3

Product from Preparation Example 4

Product from Preparation Example 5

Product from Preparation Example 6

Product from Preparation Example 7

Product from Preparation Example 8

Product from Preparation Example 9

Product from Preparation Example 10

| Product from Preparation Example 11 |  |
|---|---|

Me = methyl

What is claimed is:

1. A silylation reagent, which comprises a compound having the formula I $$(A-B_n)_mC \qquad (I)$$

wherein
- A denotes a silanyl group containing at least 2 silicon atoms in total linked to each other, but not more than 3 silicon atoms linked to each other of an unbranched chain of silicon atoms;
- B denotes a bridging group;
- C denotes a functional group which is capable of forming a covalent bond with an aromatic, aliphatic or cycloaliphatic hydroxyl group;
- n denotes 0 or 1; and
- m denotes 1 or 2.

2. A silylation reagent as claimed in claim 1, wherein the group A has the formula II

$$\begin{array}{c} a_1 \\ | \\ -Si-a_2, \\ | \\ a_3 \end{array} \qquad (II)$$

wherein
- $a_1$, $a_2$, $a_3$ each independently denote R, —SiR$_3$ and —Si$_2$R$_5$, with the proviso that at least one of $a_1$, $a_2$ or $a_3$ is —SiR$_3$ and not more than one of $a_1$, $a_2$ or $a_3$ is —Si$_2$R$_5$; and each R independently denotes (C$_1$-C$_3$)-alkyl or aryl.

3. A silylation reagent as claimed in claim 1, wherein the group B has the formula III $$-(b_1)_r-(X)-(b_2)_s- \qquad (III)$$

wherein
- $b_1$ denotes (C$_1$-C$_4$)-alkylene or a group containing at least one C—C double bond and resulting from Diels-Alder reaction of an alkadienylene, with a dienophile;
- X denotes a single bond, —O—, —S—, —SO$_2$—, —NH—, —NR$^1$—, wherein R$^1$ is a (C$_1$-C$_3$)-alkyl;

- $b_2$ denotes arylene or cycloalkylene; and
- r, s each denote 0 or 1, with the proviso that for the bridging group B the sum of the values of r and s is at least 1.

4. A silylation reagent as claimed in claim 1, wherein said group C comprises functional groups which react by additition with aliphatic or aromatic hydroxyl groups.

5. A silylation reagent as claimed in claim 4, wherein said functional group C is selected from the group consisting of thiol, hydroxyl, amino, epoxy bound via alkylene, aziridino, carboxyl, isocyanate, carbodiimide and lactone.

6. A silylation reagent as claimed in claim 2, wherein the silanyl groups according to the formula II contain two or four silicon atoms.

7. A silylation reagent as claimed in claim 1, which is resistant to radiation of a wavelength greater than 300 nm.

8. A silylation reagent as claimed in claim 2, wherein R denotes a methyl group.

9. A silylation reagent as claimed in claim 2, wherein R denotes a phenyl group.

10. A silylation reagent as claimed in claim 3, wherein said (C$_1$-C$_4$)-alkylene corresponding to $b_1$ is a C$_2$-alkylene.

11. A silylation reagent as claimed in claim 3, wherein said alkadienylene is a cycloalkadienylene containing at least 4 carbon atoms.

12. A silylation reagent as claimed in claim 11, wherein said cycloalkadienylene is cyclopentadienylene.

13. A silylation reagent as claimed in claim 3, wherein said arylene corresponding to $b_2$ is naphthylene.

14. A silylation reagent as claimed in claim 3, wherein said arylene corresponding to $b_2$ is phenylene.

15. A silylation reagent as claimed in claim 3, wherein said cycloalkylene is cyclohexylene.

16. A silylation reagent as claimed in claim 3, wherein said arylene is further substituted by at least one substitutent selected from the group consisting of (C$_1$-C$_3$)-alkyl and (C$_1$-C$_3$)-alkoxy.

17. A silylation reagent as claimed in claim 16, wherein said (C$_1$-C$_3$)-alkyl is methyl and is in the ortho position to the bond which carries the functional group.

18. A silylation reagent as claimed in claim 2, wherein said group A is selected from the group consisting of —SiR(SiR$_3$)$_2$, —Si(SiR$_3$)$_3$, and —(SiR$_2$)$_2$—SiR$_3$.

* * * * *